(12) United States Patent
Candrawinata

(10) Patent No.: US 11,930,834 B2
(45) Date of Patent: Mar. 19, 2024

(54) EXTRACTION OF POLYPHENOLIC COMPOUNDS FROM POMACE

(71) Applicant: Vincent Candrawinata, Sydney (AU)

(72) Inventor: Vincent Candrawinata, Sydney (AU)

( * ) Notice: Subject to any disclaimer, the term of this patent is extended or adjusted under 35 U.S.C. 154(b) by 649 days.

(21) Appl. No.: 15/308,175

(22) PCT Filed: May 1, 2015

(86) PCT No.: PCT/AU2015/050209
§ 371 (c)(1),
(2) Date: Nov. 1, 2016

(87) PCT Pub. No.: WO2015/164928
PCT Pub. Date: Nov. 5, 2015

(65) Prior Publication Data
US 2017/0099859 A1     Apr. 13, 2017

(30) Foreign Application Priority Data

May 2, 2014   (AU) ............................... 2014901593

(51) Int. Cl.
| | |
|---|---|
| *A23L 2/04* | (2006.01) |
| *A23L 2/02* | (2006.01) |
| *A23L 2/52* | (2006.01) |
| *A23L 5/30* | (2016.01) |
| *A23L 19/00* | (2016.01) |
| *A23L 33/105* | (2016.01) |
| *A61K 36/73* | (2006.01) |

(52) U.S. Cl.
CPC .................. *A23L 2/04* (2013.01); *A23L 2/02* (2013.01); *A23L 2/52* (2013.01); *A23L 5/32* (2016.08); *A23L 19/00* (2016.08); *A23L 33/105* (2016.08); *A61K 36/73* (2013.01); *A23V 2002/00* (2013.01); *A61K 2236/15* (2013.01); *A61K 2236/30* (2013.01); *A61K 2236/50* (2013.01); *A61K 2236/53* (2013.01)

(58) Field of Classification Search
None
See application file for complete search history.

(56) References Cited

U.S. PATENT DOCUMENTS

| | | | | |
|---|---|---|---|---|
| 5,019,412 | A * | 5/1991 | Hattori ..................... | A23G 3/52 219/680 |
| 2011/0028427 | A1* | 2/2011 | McManus ................ | A21D 2/36 514/54 |
| 2011/0152371 | A1* | 6/2011 | Rupasinghe ......... | A23D 7/0053 514/560 |
| 2011/0303524 | A1* | 12/2011 | Lee ..................... | B01D 1/0029 201/2 |

FOREIGN PATENT DOCUMENTS

| | | | |
|---|---|---|---|
| CN | 102260588 | A | 11/2011 |
| CN | 103462148 | A * | 8/2013 |
| CN | 103462148 | A | 12/2013 |
| WO | 2014174703 | A1 | 10/2014 |

OTHER PUBLICATIONS

Cam et al., Optimization of Extraction of Apple Pomace Phenolics with Water by Response Surface Methodology, 2010, J Agric Food Chem, 58: 9103-9111.*
Cilek, B., 'Microencapsulation of phenolic compounds extracted from sour cherry (*Prunus cerasus* L.) pomace', Master's thesis from Middle East Technical University, Sep. 2012, p. 20, 23.
Gonzalez-Centeno, M. R. et al., 'Effect of acoustic frequency and power density on the aqueous ultrasonic-assisted extraction of grape pomace ( *Vitis vinifera* L.)—a response surface approach', Ultrasonics Sonochemistry, 2014, vol. 21, pp. 2176-2184.
International Search Report & Written Opinion dated Jun. 16, 2015 from corresponding International PCT Application No. PCT/AU2015/050209, 15 pages.
Lohani, U. C. et al., 'Effect of Drying Methods and Ultrasonication in Improving the Antioxidant Activity and Total Phenolic Content of Apple Pomace Powder', Journal of Food Research, 2015, vol. 4, pp. 68-77.
Pan, Z., et al, "Continuous and pulsed ultrasound-assisted extractions of antioxidants from pomegranate peel," Ultrasonics Sonochemistry, 2012, vol. 19, pp. 365-372.

* cited by examiner

*Primary Examiner* — Terry A McKelvey
*Assistant Examiner* — Catheryne Chen
(74) *Attorney, Agent, or Firm* — INNOVATION CAPITAL LAW GROUP, LLP; Vic Lin

(57) ABSTRACT

Methods of extraction of one or more polyphenolic compounds from pomace are described. The invention also provides uses of the extracts in the fortification of fruit juice, vegetable juice and foods, and as an antioxidant, an anti-inflammatory and an antifungal.

22 Claims, No Drawings

EXTRACTION OF POLYPHENOLIC COMPOUNDS FROM POMACE

FIELD OF THE INVENTION

The present invention relates generally to a method of extraction of one or more polyphenolic compounds from pomace and to the uses of such extracts in the fortification of fruit juice, vegetable juice and foods, and as an antioxidant, an anti-inflammatory and an antifungal.

BACKGROUND OF THE INVENTION

When fruits and vegetables are pressed or processed for juice, oil, wine, or other products, the organic process waste generated is known as pomace. Pomace typically represents approximately 20% to 35% of the original fruit or vegetable matter and is generally composed of carbohydrates, dietary fibres and small amounts of protein. Pomace also contains the majority of the polyphenolic compounds present in fresh, unprocessed fruit and vegetables. For example, after conventional apple juice production, the amount of polyphenolic compounds in the processed apple juice is reduced by at least 58% to 95% compared to the amount of polyphenolic compounds in whole unprocessed apples. Pomace is therefore a rich source of polyphenolic compounds.

Many studies have shown that the polyphenolic compounds found in fruit and vegetables have antioxidative activity and can prevent or ameliorate oxidative stress. Oxidative stress is associated with cardiovascular diseases, respiratory disorders, neurodegenerative diseases, cancer and diabetes. Studies have also shown that polyphenolic compounds have anti-inflammatory properties and are therefore useful for treating chronic inflammatory diseases.

It is beneficial to extract polyphenolic compounds from pomace and to use them to fortify fruit juice and vegetable juice. The benefits are two-fold: using the pomace results in a reduction in the amount of waste produced during fruit and vegetable juice production; and the beneficial health properties of polyphenolic compounds are maintained in the fruit and vegetable juice.

Accordingly there is a need for a method of extracting polyphenolic compounds from pomace that is safe to the manufacturer, has low processing costs, and is free from chemical solvents and is thus both more environmentally friendly and more appealing to the consumer.

The present inventors have surprisingly found a method for extracting polyphenolic compounds from pomace comprising subjecting the pomace to microwave radiation and/or ultrasonication. The method does not use chemical solvents.

SUMMARY OF THE INVENTION

According to a first aspect of the invention there is provided a method for extracting one or more polyphenolic compounds from pomace the method comprising: a) providing a pomace; b) subjecting the pomace to ultrasonication; c) extracting the pomace to produce an extract comprising one or more polyphenolic compounds; and d) subjecting the extract to ultrasonication.

In one embodiment the method further comprises subjecting the pomace to microwave radiation before step b). In an alternate embodiment the method further comprises subjecting the pomace to microwave radiation after step b).

In some embodiments, step c), the step of extracting the pomace to produce an extract comprising one or more polyphenolic compounds is carried out and/or is prepared in, and/or comprises water.

In particular embodiments the pomace is provided as a pomace/water mixture. The ratio of pomace to water in the mixture may be from about 0.01 g/mL water to about 0.40 g/mL water. The ratio of pomace to water in the mixture may be from about 0.01 g/mL water to about 0.20 g/mL water. The ratio of pomace to water in the mixture may be from about 0.04 g/mL water to about 0.09 g/mL water.

In particular embodiments the method further comprises subjecting the pomace and/or extract to heat. The pomace is typically subjected to heating at a temperature of about 40° C. to about 100° C. for a period of time of about 10 minutes to about 50 minutes. In one embodiment the pomace may be subject to heating at a temperature of about 85° C. for a period of time of about 30 minutes. In some embodiments the method may comprise agitating the pomace and/or extract whilst subjecting the pomace and/or extract to heat. The pomace and/or extract may be heated in a water bath. The pomace and/or extract may also be heated in a flask on a hot plate with continuous stirring.

The pomace may be subject to microwave radiation for a period of time of from about 1 minute to about 5 minutes at a power between about 300 W to 1500 W. In one embodiment the pomace may be subject to microwave radiation for a period of time of about 3 minutes at a power of about 800 W.

The pomace and/or extract is typically subject to ultrasonication for about a period of time of 1 minute to about 120 minutes at a temperature about 40° C. to about 100° C. In one embodiment the pomace may be subject to ultrasonication for a period of time of about 6 minutes at a temperature of about 85° C.

In other embodiments the method further comprises cooling the pomace and/or extract. The pomace and/or extract is typically cooled to a temperature of about 5° C. to about 30° C. In one embodiment the pomace and/or extract is cooled to a temperature of about 10° C. to about 25° C.

The pomace and/or extract may be cooled in an ice bath.

In another embodiment the method further comprises filtering the treated pomace and/or extract to obtain an extract comprising the one or more polyphenolic compounds. In some embodiments the filtrate from the pomace and/or extract may be subject to centrifugation.

The pomace may be a fruit pomace or a vegetable pomace. In some embodiments the pomace may be a pomaceous fruit, a berry, a citrus fruit or a stone fruit. In particular embodiments the pomace may be from a pomaceous fruit. The pomaceous fruit may be an apple.

According to a second aspect of the invention there is provided a method for extracting one or more polyphenolic compounds from pomace the method comprising: a) providing a pomace; b) subjecting the pomace to microwave radiation; and c) subjecting the pomace to ultrasonication, to produce an extract comprising one or more polyphenolic compounds, wherein steps b) and c) are carried out in any order.

According to a third aspect of the invention there is provided a method for extracting one or more polyphenolic compounds from pomace the method comprising: a) providing a pomace; b) subjecting the pomace to microwave radiation; c) subjecting the pomace to ultrasonication; and d) subjecting the pomace to heat, to produce an extract comprising one or more polyphenolic compounds, wherein steps b) and c) are carried out in any order.

According to a fourth aspect of the invention there is provided an extract comprising one or more polyphenolic compounds obtained by the method defined in the first, second or third aspect.

According to a fifth aspect of the invention there is provided a use of an extract comprising one or more polyphenolic compounds as defined in the fourth aspect for the fortification of a fruit juice or a vegetable juice.

According to a sixth aspect there is a provided a juice produced according to the fifth aspect.

s According to a seventh aspect of the invention there is provided a use of an extract comprising one or more polyphenolic compounds as defined in the fourth aspect for the fortification of a food or a beverage.

According to an eighth aspect of the invention there is provided a food or a beverage produced according to the seventh aspect.

According to a ninth aspect of the invention there is provided a use of an extract comprising one or more polyphenolic compounds as defined in the fourth aspect as a food additive.

According to a tenth aspect of the invention there is provided a use of an extract comprising one or more polyphenolic compounds as defined in the fourth aspect as a medicament.

According to an eleventh aspect of the invention there is provided a use of an extract comprising one or more polyphenolic compounds as defined in the fourth aspect as an antioxidant.

According to a twelfth aspect of the invention there is provided a use of an extract comprising one or more polyphenolic compounds as defined in the fourth aspect as an anti-inflammatory.

According to a thirteenth aspect of the invention there is provided a use of an extract comprising one or more polyphenolic compounds as defined in the fourth aspect as an antifungal.

DETAILED DESCRIPTION OF THE INVENTION

Throughout this specification and the claims which follow, unless the context requires otherwise, the word "comprise", and variations such as "comprises" or "comprising", will be understood to imply the inclusion of a stated element, integer or step, or group of elements, integers or steps, but not the exclusion of any other element, integer or step, or group of elements, integers or steps.

In the context of this specification, the terms "a" and "an" are used herein to refer to one or to more than one (i.e. to at least one) of the grammatical object of the article. By way of example, "an element" means one element or more than one element.

In the context of this specification, the term "about," is understood to refer to a range of numbers that a person of skill in the art would consider equivalent to the recited value in the context of achieving the same function or result.

In the context of this specification, the term "pomace" refers to the solid and liquid remains of fruit and/or vegetables after pressing or processing for juice, oil, wine or other products. Pomace may include but is not limited to the skin, pulp, flesh, seeds, juice, oil and stems of the fruit or vegetable. The term "pomace" and the like are to be considered in their broadest context.

In the context of this specification, the term "extract" refers to a preparation derived from pomace produced in accordance with the invention and comprising one or more polyphenolic compounds. An extract is obtained by a process of "extraction" which will be understood by those skilled in the art as, in general terms, treatment of pomace to dissolve one or more polyphenolic compounds and where necessary to separate the same from residual unwanted pomace. An extract may be in liquid form (for example as a decoction, solution, infusion or tincture) or solid form (for example as a powder or granules).

In the context of this specification, the term "polyphenolic compounds" refers to a large group of naturally occurring compounds with structural diversity but with at least one phenolic unit and no nitrogen based groups. The person skilled in the art will appreciate that the amount and type of polyphenolic compounds will be vary depending on the source of the pomace.

In the context of the specification, the terms "microwave" and "microwave radiation" refer to electromagnetic waves with wavelengths ranging from 10 to 187 mm with a frequency range of 30 to 1.6 GHz. The terms "microwave" and "microwave radiation" and the like are to be considered in their broadest context.

In the context of this specification, the terms "fortify" and "fortification" refer to the addition of an extract of the invention comprising one or more polyphenolic compounds to a juice, a beverage, or a food to enrich and increase the level of one or more polyphenolic compounds in the juice, beverage or food, irrespective of whether or not the one or more polyphenolic compounds were originally in the juice, beverage or food, to for example, improve the nutritional quality of the juice, beverage, or food or to provide a health benefit.

In the context of this specification, the term "juice", "juices", "food", "foods", "beverage" or "beverages" include but are not limited to fruit juice, vegetable juice, health foods, functional foods and foods for specified health use. When the extracts of the present invention are used to fortify food for subjects other than humans, the term can be used to include a feedstuff.

In the context of this specification, the term "subject" includes humans, primates, livestock animals (eg. sheep, pigs, cattle, horses, donkeys), laboratory test animals (eg. mice, rabbits, rats, guinea pigs), companion animals (eg. dogs, cats) and captive wild animals (eg. foxes, kangaroos, deer). Typically, the subject is a human or a laboratory test animal. Even more typically, the subject is a human.

The present invention is predicated on the inventors' finding, as exemplified herein, that one or more polyphenolic compounds can be extracted from pomace by subjecting the pomace to ultrasonication; producing an extract comprising one or more polyphenolic compounds; and subjecting the extract to ultrasonication. In some embodiments the pomace is also subject to microwave radiation. The extracts comprising one or more polyphenolic compounds may find use in fortifying fruit or vegetable juice to, for example, enhance the clarity and/or colour of the juice and/or to increase the content of polyphenolic compounds in the juice. The extracts may also be used to fortify a beverage or food. The extracts comprising one or more polyphenolic compounds may also be used as an antioxidant, an anti-inflammatory or an antifungal. The extracts may also find use as health supplements for those who require a high level of polyphenolic compounds in their diet, for example those who wish to prevent or ameliorate a cardiovascular disease, a respiratory disorder, a neurodegenerative disease, cancer and/or diabetes.

Accordingly, one aspect of the invention provides a method for extracting one or more polyphenolic compounds from pomace the method comprising: a) providing a pomace; b) subjecting the pomace to ultrasonication; c) extracting the pomace to produce an extract comprising one or more polyphenolic compounds; and d) subjecting the extract to ultrasonication. The pomace may be subject to microwave radiation before or after b) ultrasonication. The method does not use chemical solvents. The extraction may be carried out in water.

In another aspect the invention provides a method for extracting one or more polyphenolic compounds from pomace the method comprising: a) providing a pomace; b) subjecting the pomace to microwave radiation; and c) subjecting the pomace to ultrasonication, to produce an extract comprising one or more polyphenolic compounds, wherein steps b) and c) are carried out in any order.

In another aspect the invention provides a method for extracting one or more polyphenolic compounds from pomace the method comprising: a) providing a pomace; b) subjecting the pomace to microwave radiation; c) subjecting the pomace to ultrasonication; and d) subjecting the pomace to heat, to produce an extract comprising one or more polyphenolic compounds, wherein steps b) and c) are carried out in any order.

In accordance with particular embodiments of the invention the pomace and/or extract is subject to ultrasonication for a period of time of between about 5 seconds to about 120 minutes, or more typically between about 1 minute and about 60 minutes. Alternatively, the pomace and/or extract may be subject to ultrasonication for about 1.5 minutes, 2 minutes, 2.5 minutes, 3 minutes, 3.5 minutes, 4 minutes, 4.5 minutes, 5 minutes, 5.5 minutes, 6 minutes, 6.5 minutes, 7 minutes, 7.5 minutes, 8 minutes, 8.5 minutes, 9 minutes, 9.5 minutes, 10 minutes, 10.5 minutes, 11 minutes, 11.5 minutes, 12 minutes, 12.5 minutes, 13 minutes, 13.5 minutes, 14 minutes, 14.5 minutes, 15 minutes, 15.5 minutes, 16 minutes, 16.5 minutes, 17 minutes, 17.5 minutes, 18 minutes, 18.5 minutes, 19 minutes, 19.5 minutes, 20 minutes, 20.5 minutes, 21 minutes, 21.5 minutes, 22 minutes, 22.5 minutes, 23 minutes, 23.5 minutes, 24 minutes, 24.5 minutes, 25 minutes, 25.5 minutes, 26 minutes, 26.5 minutes, 27 minutes, 27.5 minutes, 28 minutes, 28.5 minutes, 29 minutes, 29.5 minutes, 30 minutes, 30.5 minutes, 31.5 minutes, 32 minutes, 32.5 minutes, 33 minutes, 33.5 minutes, 34 minutes, 34.5 minutes, 35 minutes, 35.5 minutes, 36 minutes, 36.5 minutes, 37 minutes, 37.5 minutes, 38 minutes, 38.5 minutes, 39 minutes, 39.5 minutes, 40 minutes, 41.5 minutes, 42 minutes, 42.5 minutes, 43 minutes, 43.5 minutes, 44 minutes, 44.5 minutes, 45 minutes, 45.5 minutes, 46 minutes, 46.5 minutes, 47 minutes, 47.5 minutes, 48 minutes, 48.5 minutes, 49 minutes, 49.5 minutes, 50 minutes, 50.5 minutes, 51 minutes, 51.5 minutes, 52 minutes, 52.5 minutes, 53 minutes, 53.5 minutes, 54 minutes, 54.5 minutes, 55 minutes, 55.5 minutes, 56 minutes, 56.5 minutes, 57 minutes, 57.5 minutes, 58 minutes, 58.5 minutes, 59 minutes, or 59.5 minutes.

Those skilled in the art will appreciate that the specific power and frequency of the ultrasonication as well as the time that the pomace and/or extract is subject to ultrasonication will depend on a variety of factors including, for example, the source of the pomace, the physical nature of the pomace and/or extract (whether predominantly solid or liquid in state), the water content of the pomace and/or extract, the amount of pomace and/or extract and the stability of the pomace and/or extract. The pomace and/or extract may be subject to a single exposure of ultrasonication radiation or multiple times with the number of exposures being determined as required depending on the nature of the pomace and/or extract. In accordance with particular embodiments of the invention the pomace and/or extract is subject to ultrasonication at a temperature of between about 30° C. to about 150° C., or more typically between about 40° C. to about 100° C. Alternatively, the pomace and/or extract may be subject to ultrasonication at a temperature of about 45° C., 50° C., 55° C., 60° C., 65° C., 70° C., 75° C., 85° C., 90° C. or 95° C.

In some embodiments the pomace may be mixed with water to provide a pomace/water mixture prior to or after being subject to microwave radiation and/or ultrasonication. Those skilled in the art will appreciate that any water suitable for consumption may be used. For example, the water may be, but is not limited to, distilled water, doubly distilled water, deionised water, distilled and deionised water, boiled water, rain water, tap water or any water purified by reverse osmosis, carbon filtration, microfiltration, ultrafiltration, ultraviolet oxidation or electrodialysis. In accordance with particular embodiments of the invention the ratio of the pomace/water mixture is from about 0.01 to about 0.4 g/ml, typically between about 0.01 g/mL to about 0.2 g/mL, or more typically between about 0.04 g/mL to about 0.09 g/mL. Alternatively, the ratio of the pomace/water mixture may be about 0.045 g/mL, 0.05 g/mL, 0.055 g/mL, 0.06 g/mL, 0.065 g/mL, 0.07 g/mL, 0.075 g/mL, 0.08 g/mL, or 0.085 g/mL.

Those skilled in the art will appreciate that when used the specific power of the microwave radiation as well as the time that the pomace is subject to microwave radiation will depend on a variety of factors including, for example, the source of the pomace, the physical nature of the pomace (whether predominantly solid or liquid in state), the water content of the pomace, the amount of pomace and the stability of the pomace. The pomace may be subject to a single exposure to microwave radiation or multiple times with the number of exposures being determined as required depending on the nature of the pomace. Those skilled in the art will appreciate that microwave radiation in conventional domestic or laboratory ovens typically has a frequency of 2.45 GHz and a wavelength of 122 mm and that microwave radiation in industrial/commercial ovens typically has a frequency of 915 MHz and a frequency of 328 mm, however the microwave radiation used in the present invention is not so limited.

In accordance with particular embodiments of the invention the pomace is subject to microwave radiation for a period of time of between about 1 second to about 10 minutes, or more typically between about 1 minute and about 5 minutes. Alternatively, the pomace may be subject to microwave radiation for about 1.5 minutes, 2 minutes, 2.5 minutes, 3 minutes, 3.5 minutes, 4 minutes or 4.5 minutes.

In accordance with particular embodiments of the invention the pomace is subject to microwave radiation with a power between about 100 W to about 2000 W, or more typically between about 300 W to 1500 W. Alternatively, the pomace may be subject to microwave radiation with a power about 350 W, 400 W, 450 W, 500 W, 550 W, 600 W, 650 W, 700 W, 750 W, 800 W, 850 W, 900 W, 950 W, 1000 W, 1050 W, 1100 W, 1150 W, 1200 W, 1250 W, 1300 W, 1350 W, 1400 W or 1450 W.

In some embodiments the method for extracting one or more polyphenolic compounds comprises subjecting the pomace and/or extract to heat. In accordance with particular embodiments of the invention the pomace and/or extract is subject to heat at a temperature of between about 30° C. to about 100 C, or more typically between about 40° C. to about 100° C. Alternatively, the pomace and/or extract may be subject to heat at a temperature of about 45° C., 50° C., 55° C., 65° C., 70° C., 75° C., 85° C., 90° C. or 95° C. In accordance with particular embodiments of the invention the pomace and/or extract is subject to heat for a period of time of between about 1 minute to about 120 minutes, or more typically between about 10 minute and about 50 minutes. Alternatively, the pomace and/or extract may be subject to heat for about 15 minutes, 20 minutes, 25 minutes, 30 minutes, 35 minutes, 40 minutes or 45 minutes. In some embodiments the pomace may be subject to agitation whilst heating. The heating and/or agitation may take place in a water bath.

In another embodiment the method for extracting one or more polyphenolic compounds from pomace may further comprise cooling the pomace and/or extract. In accordance with particular embodiments of the invention the pomace and/or extract may be cooled to a temperature of about 2° C. to about 20° C., or more typically between about 5° C. to about 30° C. In one embodiment the pomace m and/or extract ay be cooled to a temperature of about 10° C. to about 25° C. Alternatively, the pomace and/or extract may be cooled until the pomace is at a temperature of about 11° C., 12° C., 13° C., 14° C., 15° C., 16° C., 17° C., 18° C., 19° C., 20° C., 21° C., 22° C., 23° C. or 24° C. The pomace may be cooled in an ice bath or left to cool to room temperature.

In another embodiment the method for extracting one or more polyphenolic compounds from pomace may further comprise filtering the treated pomace and/or extract. Those skilled in the art will appreciate that the pomace and/or extract may filtered using any manner of filtration for example, but not limited to, any type of mechanical or chemical filtration. The filtration employed may be a multi-step filtration. In particular embodiments the filtration method may be by vacuum-filtration using a double-layer cheesecloth.

In some embodiments the filtrate may be subject to centrifugation. Those skilled in the art will appreciate that the pomace may be subject to centrifugation using any manner of centrifuge for example, but not limited to, a micro-centrifuge, a high-speed centrifuge or an ultracentrifuge. Those skilled in the art will appreciate that the speed and duration of the centrifugation will depend on the nature of the pomace.

Any type of pomace may be used in the method of the invention. The pomace may comprise liquids and/or solids and may have any level of water content. The pomace may include, but is not limited to, the skin, pulp, flesh, seeds, juice, oil and stems of a fruit or vegetable. Those skilled in the art will appreciate that the invention will find use in any fruit or vegetable comprising polyphenolic compounds. Fruits rich in polyphenolic compounds include, but are not limited, to apples, apricots, blackcurrants, or redcurrants, blackberries, blood oranges, barberries, bearberries, blueberries, chokeberries, cranberries, dates, elderberries, gooseberries, grapefruit, kiwi, lemon, ligonberries, loganberries, limes, mango, mandarin, marionberries, nectarines, oranges, tangelos, tangerines, peaches, pears, plums, pomegranates, pomelos, quinces, grapes, raspberries, rhubarb, strawberries, tomatoes and cherries. Vegetables rich in polyphenolic compounds include, but are not limited to, artichokes, broccoli, celery, corn, eggplant, fennel, garlic, kale, turnip, kohlrabi, leeks, onions, parsnips, spinach, cabbage, rutabagas, scallions, shallots, capsicums, sweet potato and watercress.

In particular embodiments the pomace is from a fruit. The fruit may be from a pomaceous fruit such as, but not limited to, apples, pears or quinces. In particular embodiments the pomaceous fruit is apples. The fruit may be a berry such as, but not limited to, blackcurrants, redcurrants, blackberries, blueberries, cranberries, raspberries, strawberries, tomatoes or grapes. The fruit may be a citrus fruit such as, but not limited to, blood oranges, grapefruit, lemon, limes, mandarin, oranges, tangelos, tangerines or pomelos. The fruit may be a stone fruit such as, but not limited to, plums, cherries, peaches, nectarines, apricots and mangos.

Extracts comprising one or more polyphenolic compounds prepared by the method of the invention may find use in the fortification of a fruit juice, a vegetable juice, a beverage or a food. In particular, the extracts comprising one or more polyphenolic compounds may be used to fortify fruit or vegetable juice after the pressing/processing stage of manufacture, for example, to enhance the clarity and/or colour of the juice and/or to increase the content of polyphenolic compounds in the juice. In the production of fruit juice and vegetable juice water is often added to improve the clarity and/or standardise the colour of the juice. Where appropriate, the extracts of the invention may find use as a full or partial replacement to the addition of water to improve the clarity and/or standardise the colour of the juice.

The extracts may be conveniently incorporated in a variety of beverage and food products, nutraceutical products, medicaments, pharmaceuticals and over-the-counter formulations. The beverage and food products may be in liquid from or solid form. Specific examples of the types of beverages or foods include, but are not limited to water-based, milk-based, yoghurt-based, other dairy-based, milk-substitute based such as soy milk or oat milk, or juice-based beverages including but not limited to fruit juice and vegetable juice, and water, soft drinks, carbonated drinks, and nutritional beverages, (including a concentrated stock solution of a beverage and a dry powder for preparation of such a beverage); baked products such as crackers, breads, muffins, rolls, bagels, biscuits, cereals, bars such as muesli bars, health food bars and the like, dressings, sauces, custards, yoghurts, puddings, pre-packaged frozen meals, soups and confectioneries.

Extracts comprising one or more polyphenolic compounds prepared by the method of the invention may also find use as a food additive for example, but not limited to, as a natural alternative to synthetic antioxidants such as sodium ascorbate (E301), calcium ascorbate (E301) potassium ascorbate (E303), propyl gallate (E310), tertiary butylhydroquinone (TBHQ, E319) and butylated hydroxyanisole (BHA, E320).

Extracts comprising one or more polyphenolic compounds prepared by the method of the invention may find use as an antioxidant and/or as an anti-inflammatory and/or as an antifungal. The extracts may be provided in any form, for example as a liquid or a powder. The extracts may be added to any type of drink or food product (for example fruit juice, vegetable juice, water, or yoghurt) and consumed there after. In another embodiment, the extracts may simply be consumed as a fluid or powder in the absence of a liquid drink or additional food product.

In some embodiments the extracts comprising one or more polyphenolic compounds may be conveniently presented and consumed as a medicament and/or a health supplement in a dosage form prepared by any of the methods well known in the art. The methods may include the step of bringing the extract into association with a carrier which constitutes one or more accessory ingredients, such as maltodextrin, dried pomace and/or plant fibre. In general, oral compositions are prepared by uniformly and intimately bringing into association the extract with a liquid carrier or finely divided solid carrier, or both and then, if necessary, shaping the product into the desired composition.

Compositions suitable for oral administration may be presented as discrete units (i.e. dosage forms) such as gelatine or HPMC capsules, cachets or tablets, each containing a predetermined amount of each component of the composition as a powder, granules, as a solution or a suspension in an aqueous liquid or a non-aqueous liquid, or as an oil-in-water liquid emulsion or a water-in-oil liquid emulsion.

When the extracts are formulated as capsules, the components of the extract may be formulated with one or more pharmaceutically acceptable carriers and/or excipients such as starch, lactose, microcrystalline cellulose, silicon dioxide, maltodextrin, dried pomace and/or plant fibre. Additional ingredients may include lubricants such as magnesium stearate and/or calcium stearate.

Tablets may be prepared by compression or moulding, optionally with one or more accessory ingredients. Compressed tablets may be prepared by compressing in a suitable machine the components of the composition in a free-flowing form such as a powder or granules, optionally mixed with a binder, lubricant (for example magnesium stearate or calcium stearate), inert diluent or a surface active/dispersing agent. Moulded tablets may be made by moulding a mixture of the powdered composition moistened with an inert liquid diluent, in a suitable machine. The tablets may optionally be coated, for example, with an enteric coating and may be formulated so as to provide slow or controlled release of the extracts therein.

Those skilled in the art will appreciate that single or multiple administrations can be carried out with dose levels and pattern being determined as required depending on the circumstances and the individual to be treated. Suitable dosage regimes can readily be determined by the skilled addressee. A broad range of doses may be applicable. Dosage regimens may be adjusted to provide the optimum therapeutic response. Those skilled in the art will appreciate that the exact amounts and rates of administration of the extracts will depend on a number of factors such as the particular composition being administered, the age, body weight, general health, sex and dietary requirements of the subject, as well as any drugs or agents used in combination or coincidental with the compositions. For example, several divided doses may be administered hourly, daily, weekly, monthly or at other suitable time intervals or the dose may be proportionally reduced as indicated by the exigencies of the situation. Those skilled in the art will, by routine trial and experimentation, be capable of determining suitable dosage regimes on a case-by-case basis The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The present invention will now be described with reference to the following specific examples, which should not be construed as in any way limiting the scope of the invention.

EXAMPLES

Example 1—Extraction of Polyphenolic Compounds from Apple Pomace

Apple pomace was sourced from Appledale Processors Co-op. Ltd., Orange, NSW, Australia. The pomace was homogenised and stored at −15° C. until use. Chemical reagents were all of analytical grade and were purchased from Sigma Aldrich Laboratory Chemicals (Castle Hill, NSW, Australia). Deionised water was prepared on the day of use with a Millipore Milli-Q water purification system (Millipore Australia, North Ryde, NSW, Australia).

Samples of 5 g of apple pomace were added to 62.5 mL deionised water (ratio 0.08 g of pomace per mL of water). Samples of apple pomace/water mixture were also prepared with ratios of 0.04 to 0.09 g of pomace per mL of water. The resulting pomace/water mixtures were subject to the following:

I. placed in a microwave in a closed system for 1 minute to 3 minutes with the microwave output power set at 1 (400 W), 2 (600 W) or 3 (800 W);
II. placed in an ultrasonic water bath maintained at 85° C. for 2 minutes to 6 minutes (UltraSONIK 57X NEY sonifier (Extech Equipment Pty. Ltd., Melbourne, VIC, Australia);
III. placed in a shaking water bath maintained at 85° C. to 95° C. for 15 minutes to 30 minutes
IV. placed in an ice bath until the temperature of the mixture was between 10° C. and 25° C.;
V. vacuum-filtered using a double-layer cheesecloth; and
VI. the filtrate centrifuged at 12,100×g (Beckman J2-AC centrifuge, Beckman Instruments Inc., California, USA) to provide a water extract of pomace comprising polyphenolic compounds.

As a control, 5 g of apple pomace was added to 20 mL analytical grade methanol and placed in an ultrasonic water bath for 20 minutes followed by vacuum-filtration through a double-layer cheesecloth followed by centrifugation at 12,100×g to provide a methanol extract of pomace comprising polyphenolic compounds.

All extracts were analysed for total phenolic content and antioxidant activity using the following assays.

Total Phenolic Content Assay

The total phenolic content of the extracts was measured by an assay based on a method established by Folin and Ciocalteu (The Journal of Biological Chemistry. 1927; 73(2): 627-50) adapted from Swain and Hillis (Journal of the Science of Food and Agriculture. 1959; 10(1): 63-8) and Thaipong et al. (Journal of Food Composition and Analysis. 2006; 19: 669-75) with minor modifications as follows. 150 μL of water or methanol extract comprising polyphenolic compounds was mixed with 150 μL of 0.25 N Folin Ciocalteu reagent. The resulting mixture was left to react for 2 minutes before adding 2400 μL of 5% (wv$^{-1}$) sodium carbonate solution. The mixture was then left to incubate for 1 h. The results from the total phenolic content assay are expressed in gallic acid equivalents (GAE, μg g$^{-1}$ fresh pomace).

Antioxidant Activity Assays

The antioxidant activity of the extracts was measured using three different assays: 1) DPPH assay; 2) FRAP assay; and 3) ABTS assay. The DPPH assay was adapted from Brand-Williams et al. Lebensmittel-Wissenschaft and Technologie/Food Science and Technology. 1995; 28: 25-30) and Thaipong et al. (Journal of Food Composition and Analysis. 2006; 19: 669-75) with some modifications. The incubation time was set for 30 minutes. The FRAP assay was performed according to Benzie and Strain (Analytical Biochemistry. 1996; 239(1): 70-6) and Thaipong et al. (Journal of Food Composition and Analysis. 2006; 19: 669-75). The ABTS assay was based on the method described in Arnao et al. (Food Chem. 2001; 73: 239-244.) and Thaipong et al. (Journal of Food Composition and Analysis. 2006; 19: 669-75). The results from the antioxidant activity assays are expressed in Trolox equivalents (TE, μg g$^{-1}$ fresh pomace). All extractions and measurements were performed in triplicate.

The data generated from the experiments to measure the total phenolic content and antioxidant activity of the extracts were subject to analysis of variance (ANOVA) using Statistical Package for the Social Science (SPSS). The significance of the difference between means was determined by one-way ANOVA with Bonferroni post-hoc tests (p<0.05).

Results

Table 1 show the results obtained with the control samples of apple pomace in methanol.

TABLE 1

| Total Phenolics (GAE[1]) | DPPH (TE[1]) | FRAP (TE[1]) | ABTS (TE[1]) |
|---|---|---|---|
| 1789 | 2021 | 1635 | 2805 |

[1]in μg g$^{-1}$ fresh pomace

Table 2 shows that a method of extraction performed with a microwave power of 800 W for 3 minutes followed by ultrasonication for 4 minutes provides an extract comprising one or more polyphenolic compounds with the highest total phenolic content and the highest levels of antioxidant activity. The experimental runs were coded and randomised to minimise the effects of unexpected variability or bias in the observed responses. The quality of the fitted model was expressed by the coefficient of determination $R^2$ value and the statistical significance was determined by an F-test (p<0.05).

TABLE 2

| Microwave Time (min) | Microwave Power[1] | Ultrasound Time (min) | Total Phenolics (GAE[2]) | DPPH (TE[2]) | FRAP (TE[2]) | ABTS (TE[2]) |
|---|---|---|---|---|---|---|
| 1 | 1 | 4 | 833 | 1026 | 944 | 1493 |
| 2 | 2 | 4 | 825 | 1031 | 925 | 1657 |
| 3 | 2 | 6 | 1034 | 1293 | 1266 | 2127 |
| 2 | 3 | 6 | 1012 | 1282 | 1119 | 1903 |
| 3 | 1 | 4 | 831 | 1035 | 885 | 1623 |
| 2 | 2 | 4 | 849 | 1060 | 906 | 1585 |
| 3 | 3 | 4 | 1367 | 1711 | 1470 | 2577 |
| 2 | 1 | 6 | 863 | 1078 | 959 | 1617 |
| 1 | 3 | 4 | 922 | 1153 | 1035 | 1894 |
| 1 | 2 | 6 | 812 | 1003 | 938 | 1512 |
| 3 | 2 | 2 | 1015 | 1248 | 1172 | 1927 |
| 1 | 2 | 2 | 1048 | 1308 | 1176 | 1865 |
| 2 | 2 | 4 | 930 | 1158 | 1072 | 1834 |
| 2 | 3 | 2 | 1040 | 1279 | 1182 | 2025 |
| 2 | 1 | 2 | 768 | 945 | 825 | 1513 |

[1]Microwave power output: 1 = 400 W, 2 = 600 W, and 3 = 800 W.
[2]in μg g$^{-1}$ fresh pomace Table 3 shows that a method of extraction performed with heating the pomace to a temperature of 85° C. for 30 minutes provides extracts comprising one or more polyphenolic compounds with the highest total phenolic content and the highest levels of antioxidant activity. The experimental data were fitted into the second order polynomial model and the regressions of the obtained equations were evaluated using variance analysis using ANOVA (Table 4). The models were statistically significant with p<0.05 at 95% confidence, while the lack of fit values were not significant. The values of $R^2$>0.85 indicated a good fit of the models for responses, which is also shown by the lower residue values.

TABLE 3

| Time (min) | Temperature (° C.) | Pomace:Water (g/mL) | Phenolics (GAE[2]) | DPPH (TE[2]) | FRAP (TE[2]) | ABTS (TE[2]) |
|---|---|---|---|---|---|---|
| 23 | 90 | 0.065 | 953 | 1166 | 1055 | 1828 |
| 35 | 90 | 0.065 | 1086 | 1423 | 1264 | 2071 |
| 23 | 90 | 0.065 | 958 | 1166 | 1046 | 1828 |
| 15 | 95 | 0.050 | 1024 | 1295 | 1119 | 1960 |
| 23 | 90 | 0.065 | 1037 | 1329 | 1151 | 1973 |
| 23 | 90 | 0.065 | 925 | 1149 | 1039 | 1759 |
| 30 | 85 | 0.080 | 1127 | 1454 | 1344 | 2174 |
| 23 | 90 | 0.090 | 881 | 1124 | 1017 | 1682 |
| 30 | 95 | 0.050 | 1122 | 1440 | 1265 | 2156 |
| 15 | 95 | 0.080 | 892 | 1150 | 1025 | 1720 |
| 15 | 85 | 0.080 | 879 | 1134 | 968 | 1673 |
| 23 | 90 | 0.040 | 1166 | 1442 | 1246 | 2248 |
| 23 | 82 | 0.065 | 995 | 1339 | 1144 | 1908 |
| 23 | 90 | 0.065 | 957 | 1154 | 991 | 1827 |
| 10 | 90 | 0.065 | 833 | 1007 | 896 | 1593 |
| 23 | 90 | 0.065 | 955 | 1132 | 1015 | 1799 |
| 23 | 98 | 0.065 | 1138 | 1527 | 1426 | 2207 |
| 30 | 85 | 0.050 | 1258 | 1654 | 1453 | 2416 |
| 15 | 85 | 0.050 | 1074 | 1324 | 1156 | 2049 |
| 30 | 95 | 0.080 | 1119 | 1510 | 1393 | 2144 |

[2]in μg g$^{-1}$ fresh pomace

TABLE 4

| | Value predicted | | | |
|---|---|---|---|---|
| Constant coefficient | TPC | DPPH | FRAP | ABTS |
| Model | 867.97 | 1082.79 | 967.97 | 1691.98 |
| MT | 79.09 | 99.68 | 87.65 | 186.32 |
| MP | 130.79 | 167.72 | 149.04 | 269.04 |
| UT | — | — | — | — |
| MT*MP | 111.74 | 137.34 | 123.51 | — |
| MT*UT | — | — | — | — |
| MP*UT | — | — | — | — |
| MT*MT | — | — | 115.98 | — |
| MP*MP | — | — | — | — |
| UT*UT | — | — | — | — |
| $R^2$ | 0.9100 | 0.8836 | 0.8722 | 0.8739 |
| Value F of model | 5.5269 | 8.4338 | 7.5821 | 7.7027 |
| Value F lack of fit | 2.5767 | 1.5258 | 3.2953 | 3.6531 |
| Valor p of model | 0.0372 | 0.0453 | 0.0149 | 0.0163 |
| Valor p lack of fit | 0.2919 | 0.2455 | 0.7831 | 0.5713 |
| SD residual (% of mean) | 8.1137 | 8.6382 | 6.7991 | 6.8155 |

Table 5 shows a comparison between the predicted results and actual or real experimental results for the following parameters or optimum conditions (OP): microwave time 3 minutes, microwave power 3 (800 W), ultrasound time 3 minutes, and water bath for 30 minutes at a temperature of 85° C. (pomace:water ratio 0.05 g/mL) and three corroborative points (CB): CB1 (microwave time 2 minutes, microwave power 2 (600 W), ultrasound time 4 minutes), CB2 (microwave time 1 minutes, microwave power 2 (600 W), ultrasound time 6 minutes) and CB3 (microwave time 3 minutes, microwave power 1 (400 W), ultrasound time 2 minutes) The statistical analysis indicates that the assay values from both pre-treatments and extraction experiments, the predictive models and methods are reliable and reproducible with a relatively low value of variation coefficients (% CV).

TABLE 5

| | FC (µg GAE g − 1) | | | DPPH (µg TE g − 1) | | |
|---|---|---|---|---|---|---|
| | Predicted | Real | CV (%) | Predicted | Real | CV (%) |
| OP | 1345.19 | 1312.08 ± 19.50 | 2.46 | 1697.82 | 1669.88 ± 8.58 | 1.65 |
| CB1 | 867.97 | 840.83 ± 5.21 | 3.13 | 1082.79 | 1035.47 ± 10.15 | 4.37 |
| CB2 | 816.15 | 776.05 ± 6.76 | 4.91 | 1010.42 | 965.04 ± 4.85 | 4.49 |
| CB3 | 1316.49 | 1255.11 ± 11.65 | 4.66 | 1618.97 | 1549.36 ± 12.74 | 4.30 |

| | FRAP (µg TE g − 1) | | | ABTS (µg TE g − 1) | | |
|---|---|---|---|---|---|---|
| | Predicted | Real | CV (%) | Predicted | Real | CV (%) |
| OP | 1521.62 | 1502.65 ± 4.23 | 1.25 | 2567.65 | 2441.84 ± 10.45 | 4.90 |
| CB1 | 967.97 | 924.68 ± 6.38 | 4.47 | 1691.98 | 1618.28 ± 3.49 | 4.36 |
| CB2 | 957.98 | 925.61 ± 7.93 | 3.38 | 1511.74 | 1457.29 ± 4.85 | 3.60 |
| CB3 | 1473.10 | 1411.66 ± 8.84 | 4.17 | 2446.32 | 2345.91 ± 10.39 | 4.10 |

Example 2—Extraction of Polyphenolic Compounds from Apple Pomace with Post-Extraction Ultrasonication Apple pomace was sourced, homogenised and stored as in Example 1. Chemical reagents were all of analytical grade and were purchased from Sigma Aldrich Laboratory Chemicals (Castle Hill, NSW, Australia). Deionised water was prepared on the day of use with a Millipore Milli-Q water purification system (Millipore Australia, North Ryde, NSW, Australia).

Samples of 100 g of apple pomace were added to 1000 mL deionised water (ratio 0.1 g of pomace per mL of water). The resulting pomace/water mixtures were subject to the following:
I. placed in an ultrasonic water bath maintained at 60° C. for 15 minutes to 30 minutes (UltraSONIK 57X NEY sonifier (Extech Equipment Pty. Ltd., Melbourne, VIC, Australia);
II. placed in a shaking water bath maintained at 85° C. to 95° C. for 15 minutes to 30 minutes
III. placed in an ice bath until the temperature of the mixture was between 10° C. and 25° C.;
IV. vacuum-filtered using a double-layer cheesecloth; and
V. the filtrate placed in an ultrasonic water bath at room temperature for 5 minutes to 60 minutes (UltraSONIK 57X NEY sonifier (Extech Equipment Pty. Ltd., Melbourne, VIC, Australia);

The extracts were analysed for total phenolic content and antioxidant activity using the assays described in Example 1.

Results

Table 6 shows that post extraction ultrasonication of the pomace extract in a water bath at room temperature for 5 minutes to 60 minutes provides extracts comprising one or more polyphenolic compounds with higher antioxidant activity than with no post extraction ultrasonication due to increased unconjugated polyphenolic compounds.

TABLE 6

| Ultrasound Time (min) | Total Phenolics (GAE$^2$) | DPPH (TE$^2$) | FRAP (TE$^2$) | ABTS (TE$^2$) |
|---|---|---|---|---|
| 0 | 1122.50 | 1445.07 | 1288.60 | 2167.10 |
| 5 | 1143.25 | 1507.37 | 1346.69 | 2275.38 |
| 10 | 1161.27 | 1537.63 | 1378.10 | 2306.84 |
| 15 | 1159.67 | 1665.57 | 1482.82 | 2494.97 |
| 30 | 1163.87 | 1738.70 | 1556.69 | 2637.95 |
| 45 | 1155.22 | 1758.03 | 1566.88 | 2703.77 |
| 60 | 1137.30 | 1776.03 | 1603.44 | 2733.49 |

The claims defining the invention are as follows:

1. A method for extracting one or more polyphenolic compounds from pomace the method comprising:
    a) providing a pomace;
    a1) mixing the pomace with water, as the only added solvent in the method, to provide a pomace/water mixture, wherein ratio of the pomace/water mixture is from 0.01 g/mL to 0.40 g/mL;
    a2) subjecting the pomace/water mixture to microwave radiation;
    b) subjecting the pomace/water mixture to ultrasonication;
    c) separating the solids from the pomace/water mixture from steps a2 and b) to produce a solution comprising one or more polyphenolic compounds; and
    d) subjecting the solution to ultrasonication to form a final solution.

2. The method according to claim 1, further comprising subjecting the pomace to heat.

3. The method according to claim 1, further comprising cooling the pomace.

4. The method according to claim 1, wherein the separation comprises filtering the pomace.

5. The method according to claim 4, wherein the separation comprises centrifuging the filtrate from the pomace.

6. The method according to claim 1, wherein the pomace/water mixture is subject to microwave radiation for a period of time from 1 minute to 5 minutes at a power between 300 W to 1500 W.

7. The method according to claim 1, wherein the pomace/water mixture is subject to microwave radiation for a period of time of 3 minutes at a power of 800 W.

8. The method according to claim 1, wherein the pomace/water mixture and/or extract is subject to ultrasonication for a period of time of 1 minute to about 120 minutes at a temperature between 40° C. to 100° C.

9. The method according to claim 1, wherein the pomace/water mixture is subject to ultrasonication for a period of time of 6 minutes at a temperature of 85° C.

10. The method according to claim 2, wherein the pomace is subject to heat at a temperature of 40° C. to 100° C. for a period of time of 10 minutes to 50 minutes.

11. The method according to claim 2, wherein the pomace is subject to heat at a temperature of 85° C. for a period of time of 30 minutes.

12. The method according to claim 2, further comprising agitating the pomace whilst subjecting the pomace to heat.

13. The method according to claim 1, wherein the ratio of the pomace/water is from 0.01 g/mL to 0.20 g/mL.

14. The method according to claim 1, wherein the ratio of the pomace/water is from 0.04 g/mL to 0.09 g/mL.

15. The method according to claim 3, wherein the pomace is cooled until the pomace is at a temperature of 5° C. to 15° C.

16. The method according to claim 3, wherein the pomace is cooled until the pomace is at a temperature of 10° C. to 12° C.

17. The method according to claim 1, wherein the pomace is a fruit pomace or a vegetable pomace.

18. The method according to claim 1, wherein the pomace is from a pomaceous fruit, a berry, a citrus fruit or a stone fruit.

19. The method according to claim 1, wherein the pomace is from a pomaceous fruit.

20. The method according to claim 19, wherein the pomaceous fruit is apple.

21. A method for extracting one or more polyphenolic compounds from pomace the method comprising:
   a) providing a pomace;
   a1) mixing the pomace with water, as the only added solvent in the method, to provide a pomace/water mixture;
   b) subjecting the pomace/water mixture to microwave radiation; and
   c) subjecting the pomace/water mixture from step b) to ultrasonication, to produce an ultrasonicated mixture comprising one or more polyphenolic compounds;
   d) separating the solids from the ultrasonicated mixture to provide a solution comprising one or more polyphenolic compounds; and
   e) subjecting the solution to ultrasonication.

22. A method for extracting one or more polyphenolic compounds from pomace the method comprising:
   a) providing a pomace;
   a1) mixing the pomace with water, as the only added solvent in the method, to provide a pomace/water mixture, wherein the ratio of the pomace/water mixture is from 0.01 g/mL to 0.40 g/mL;
   b) subjecting the pomace/water mixture to microwave radiation;
   c) subjecting the pomace/water mixture from step b) to ultrasonication; and
   d) subjecting the pomace/water mixture from step c) to heat, to produce an ultrasonicated and heated mixture comprising one or more polyphenolic compounds;
   e) separating the solids from the ultrasonicated and heated mixture to form a solution;
   f) subjecting the solution to ultrasonication.

* * * * *